United States Patent [19]

Matsuno et al.

[11] 4,189,485
[45] Feb. 19, 1980

[54] PURINE DERIVATIVES

[75] Inventors: Toshimi Matsuno, Suita; Kin-ichi Imai, Toyonaka, both of Japan

[73] Assignee: Takeda Chemical Industries, Ltd., Osaka, Japan

[21] Appl. No.: 931,437

[22] Filed: Aug. 7, 1978

[30] Foreign Application Priority Data

Aug. 23, 1977 [JP] Japan .................. 52-101349
Apr. 7, 1978 [JP] Japan .................. 53-041470

[51] Int. Cl.² .................................. C07D 473/34
[52] U.S. Cl. .............................. 424/253; 544/277
[58] Field of Search ................ 544/277; 424/253

[56] References Cited

U.S. PATENT DOCUMENTS

| | | | |
|---|---|---|---|
| 3,846,426 | 11/1974 | Lira et al. | 544/277 |
| 4,098,787 | 7/1978 | Tull et al. | 544/277 |
| 4,100,159 | 7/1978 | Zwan | 544/277 |

*Primary Examiner*—Nicholas S. Rizzo
*Attorney, Agent, or Firm*—Wenderoth, Lind & Ponack

[57] ABSTRACT

Novel purine derivatives of the formula:

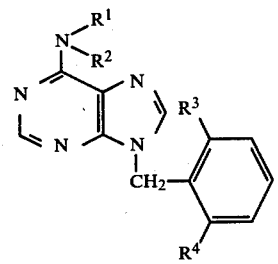

wherein $R^1$ is hydrogen or alkyl of 1 to 3 carbon atoms, $R^2$ is alkyl of 1 to 3 carbon atoms or allyl, and $R^3$ and $R^4$, respectively, mean halogen, and their acid addition salts are provided. These compounds have anticoccidial activity and are useful for treating caecal and/or intestinal coccidiosis in poultry and domestic animals.

20 Claims, No Drawings

PURINE DERIVATIVES

This invention relates to novel purine derivatives having anticoccidial activity.

Coccidiosis is an infectious disease in poultry and domestic animals, which is caused by parasitic protozoas and is responsible for diarrhea and nutritional disturbance. Frequently, the disease plays a great havoc with chickens, quails, turkeys, rabbits, goats, sheep, cattle and other poultry or animals.

As regards poultry, 9 different parasitic protozoan species of the genus Eimeria (hereinafter abbreviated as "E") have been identified in chickens. Important species of this genus are E. tenella, E. acervulina, E. maxima, E. necatrix and E. brunetti, and, among those species, E. tenella and E. necatrix, in particular, cause the most serious coccidiosis which, if untreated, would cause reductions in body weight and feed efficiency and, ultimately, cause deaths. Thus, coccidiosis in chickens, for instance, has been inflicting a considerable damage on the poultry industry and, heretofore, a variety of compounds have been developed and sold for the prevention and treatment of coccidiosis. However, drugs currently available have several disadvantages such as high toxicity and the objectionable odor which poultry meat will pick up. Moreover, the emergence of coccidia resistant to such drugs prevents the drugs from displaying their expected activity. Under the circumstances the development of a new drug active against the entire spectrum of coccidial protozoa has been much awaited.

In view of the above situation, we conducted an intensive research and discovered novel purine derivatives which are able to display positive prophylactic and therapeutic activity against coccidiosis and which are free from the disadvantages associated with the conventional anticoccidial drugs. The above finding was followed by further research which culminated in the completion of this invention.

This invention is, therefore, directed to purine derivatives having the formula:

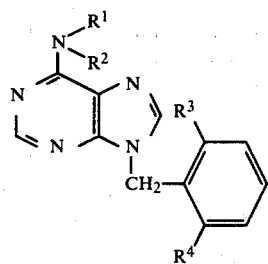

wherein $R^1$ is hydrogen or alkyl of 1 to 3 carbon atoms, $R^2$ is alkyl of 1 to 3 carbon atoms or allyl, and $R^3$ and $R^4$, respectively, represent halogen, and acid addition salts thereof.

Referring to the above formula (I), the alkyl group of 1 to 3 carbon atoms as represented by $R^1$ and $R^2$, respectively, may for example be methyl, ethyl, propyl or isopropyl. The halogen atoms which are designated by $R^3$ and $R^4$, respectively, may for example be chlorine or fluorine and may be the same or different halogens.

The following is a partial list of the purine derivatives having the formula (I):

9-(2-Chloro-6-fluorobenzyl)-6-methylaminopurine;
9-(2,6-Dichlorobenzyl)-6-methylaminopurine;
9-(2-Chloro-6-fluorobenzyl)-6-dimethylaminopurine;
9-(2,6-Dichlorobenzyl)-6-dimethylaminopurine;
9-(2-Chloro-6-fluorobenzyl)-6-ethylaminopurine;
9-(2,6-Dichlorobenzyl)-6-ethylaminopurine,
9-(2-Chloro-6-fluorobenzyl)-6-diethylaminopurine;
9-(2,6-Dichlorobenzyl)-6-diethylaminopurine;
9-(2-Chloro-6-fluorobenzyl)-6-n-propylaminopurine;
9-(2,6-Dichlorobenzyl)-6-isopropylaminopurine;
6-Allylamino-9-(2-chloro-6-fluorobenzyl)purine;
6-Allylamino-9-(2,6-dichlorobenzyl)purine.

Among those purine derivatives (I), the compounds in which $R^1$ is hydrogen or methyl; $R^2$ is methyl or ethyl, especially methyl; $R^3$ is chlorine and $R^4$ is chlorine or fluorine, especially fluorine; are preferred compounds and the compound in which $R^1$ is hydrogen, $R^2$ is methyl, $R^3$ is chlorine and $R^4$ is fluorine, namely 9-(2-chloro-6-fluorobenzyl)-6-methylaminopurine, is the most desirable.

The purine derivative (I) may be in the form of a salt which may for example be an acid addition salt with hydrochloric acid, sulfuric acid or the like.

The purine derivative (I) according to this invention can be produced, for example, by reacting a compound of the formula:

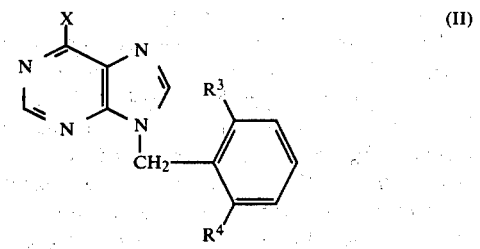

wherein $R^3$ and $R^4$ have the same meanings as defined hereinbefore and X is halogen or methylthio, with an amine of the formula:

wherein $R^1$ and $R^2$ have the same meanings as defined hereinbefore.

The starting compound (II) employed in the above reaction can be prepared by a process disclosed in Journal of Medicinal Chemistry 14, 809(1971) or analogous processes. The amine of the formula (III) may for example be methylamine, dimethylamine, ethylamine, diethylamine, propylamine, isopropylamine allylamine, etc. The halogen atom X may for example be chlorine or bromine.

The above reaction is normally carried out in a solvent inert to the reaction, such as an alcohol (e.g. methanol or ethanol), dimethylformamide or the like, at a temperature from about 60° to 200° C. The ratio of (III) to (II) may normally be about 1 to 5 equivalents, although (III) may be employed in excess, if necessary.

The compound (I) in which $R^1$ is hydrogen and $R^2$ is methyl, i.e. a compound of the formula:

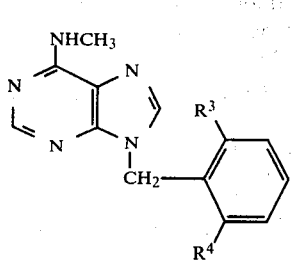

wherein $R^3$ and $R^4$ have the same meanings as defined hereinbefore, can be produced, for example, by reacting a compound of the formula:

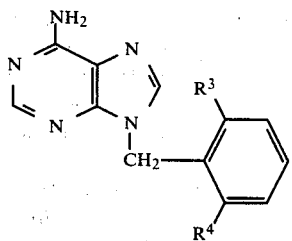

wherein $R^3$ and $R^4$ have the same meanings as defined hereinbefore, with methyl iodide, and then subjecting the obtained compound to Dimroth rearrangement reaction under basic condition.

The starting compound (IV) can be prepared, for example, by a procedure disclosed in Japanese Patent Application Laid-Open No. 29394/1972 (U.S. Pat. No. 3,846,426). The reaction of the compound (IV) with methyl iodide is normally conducted in a solvent such as N,N-dimethylformamide, N,N-dimethylacetamide or the like, at room temperature. The amount of methyl iodide is 1 to 10 molar equivalents to that of the compound (IV). The methylation occurs at the 1-position of the compound (IV). Dimroth rearrangement of the 1-methyl derivative of the compound (IV) thus obtained, proceeds readily in the presence of a base to give the compound (I'). As the base employed in this reaction, there may be mentioned alkali metal hydroxides such as sodium hydroxide or potassium hydroxide; amines such as methylamine or dimethylamine; and alkali metal alkoxides such as sodium methoxide or sodium ethoxide. Usually the base mentioned above may be employed in excess. The reaction is preferably carried out in the presence of a solvent, for example, alcohols such as methanol, ethanol or 2-methoxyethanol; or water at room temperature.

The purine derivative (I) can be produced also by reacting a compound of the formula:

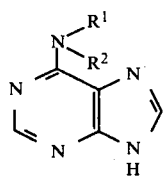

wherein $R^1$ and $R^2$ have the same meanings as defined hereinbefore, with a compound of the formula:

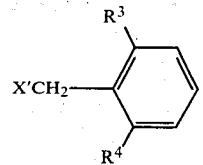

wherein $R^3$ and $R^4$ have the same meanings as defined hereinbefore, and X' is halogen, in the presence of a base.

In the above formula (VI), the halogen atom X' may for example be chlorine or bromine. The base employed in this reaction may for example be alkali metal carbonates (e.g. sodium carbonate, potassium carbonate), alkali metal hydroxides (e.g. sodium hydroxide, potassium hydroxide), tertiary-amines (e.g. trimethylamine, triethylamine, tri-n-propylamine), alkali metal alkoxides (e.g. sodium methoxide, sodium ethoxide, potassium tertiary-butoxide), sodium hydride or the like. The amount of the base is preferably about 1 to 4 molar equivalents to that of the compound (V). The introduction of the compound (VI) into the 9-position of the compound (V) was not successful until said base came to be employed as a catalyst-like agent, bringing about a high yield of the resulting product. To state it otherwise, in case of employing no base, the compound (VI) is generally introduced into the 3-position of the compound (V). This reaction is normally carried out in a solvent inert to the reaction such as N,N-dimethylformamide, N,N-dimethylacetamide, acetonitrile, nitromethane, alcohols (e.g. methanol, ethanol, tertiary-butanol) or the like, at a temperature from room temperature to about 150° C., preferably at a temperature from about 50° to about 110° C. The amount of the compound (VI) is preferably 1 to 4 molar equivalents to that of the compound (V).

The purine derivative (I) produced by any of the above reactions can be isolated from the reaction mixture by a conventional separation-purification procedure (e.g. concentration, filtration, recrystallization). The purine derivative (I) may be isolated also as the acid addition salt mentioned hereinbefore by a conventional procedure.

The purine derivatives (I) and salts thereof, which are provided by this invention, have excellent anticoccidial activity and are low in toxicity. Therefore, these compounds are of value as agents for the prophylaxis and treatment of coccidiosis in poultry and domestic animals (e.g. chickens, turkeys, cattle, etc.). Such anticoccidial agents are prepared by formulating a compound (I) or a salt thereof into such application forms as powders, dusts, granules, tablets, solutions, capsules, etc., either as undiluted or as diluted with a solid or liquid diluent, or by adding said compound (I) or salt to feeds, drinking water or other material either directly on as previously dispersed in a diluent. The above-mentioned diluent may be any material that is physiologically harmless per se and, preferably, a material or materials which can be of use as feeds or components of feeds. As examples of said solid diluent there may be mentioned barley meal, wheat meal, corn meal, soybean cake, soybean meal, rape seed cake, rice hulls, rice bran, extracted rice bran, sweet potato meal, white potato meal, soybean curd refuse, starch, lactose, sucrose, glucose, fructose, yeast, spent yeast, fish meal and so on, while water, physiological saline and physiologically acceptable organic solvents may be mentioned as examples of said liquid diluent. In addition, other suitable adjuvants or auxiliary agents such as emulsifiers, dispersants, suspension aids, wetting agents, solubilizers, etc. may further be incorporated in suitable amounts. It is also possible to incorporate preservatives, fungicides, antibiotics, enzyme preparations, lactobacillus preparations and so forth, or to admix other anticoccidial agents, sulfa drugs, vitamin preparations, etc. with the compositions according to this invention.

The anticoccidial composition containing a purine derivative (I) or a salt thereof, which is provided by this invention, is very highly effective in the prophylaxis and treatment of coccidiosis in poultry and domestic animals and is low in toxicity. Therefore, the dosage may be optionally selected according to such factors as the species of poultry or animal, body weight, age and object of application. Thus, for the prophylaxis or treatment of chicken coccidiosis, for instance, it is desirably applied at the dose level, as compound (I), of about 0.4 to 100 mg/kg/day or, preferably, about 0.8 to 30 mg/kg/day. In a practically convenient procedure, an anticoccidial composition of this invention is added to the poultry ration at the level, as compound (I), of about 0.0004 to 0.1 weight percent or, preferably, about 0.0008 to 0.03 weight percent.

As will be apparent from the experimental data given hereinafter, the anticoccidial agent according to this invention inhibits all haemorrhages, infection deaths and pathological changes in the intestines and produces significant gains in body weight, to mention but a few of its superior effects, even at very low concentrations.

The following are experimental data illustrating the effectiveness of the anticoccidial agent of this invention as found in chicks.

It should be understood that the term "uninfected control" means "uninfected, unmedicated control", and the term "infected control" means "infected, unmedicated control".

EXPERIMENTAL DATA 1

Test materials and testing procedures (1) Test compounds
Compound 1: 9-(2-Chloro-6-fluorobenzyl)-6-methylaminopurine
Compound 2: 9-(2,6-Dichlorobenzyl)-6-dimethylaminopurine.

(2) Ratio of each test compound to feed
To aliquots of a starter ration which was free from any anticoccidial agent (the composition of this ration is given in Table 2), there were added 0.009 weight % of compound 1 and 0.0125 weight % of compound 2, respectively, as final concentrations.

(3) Testing procedures
Nine days old White Leghorn male chicks, in groups of 3 birds, were reared on the basal feeds each containing either one of the above test compounds and at 24 hours after the start of dosing, mature oocysts of *Eimeria tenella* were inoculated directly into the crop of each bird, the inoculum size being 50,000 oocysts per bird. Control chicks, in groups of 3 birds, were reared on the basal feed containing neither of the test compounds and, after the same time interval as mentioned above, infected with coccidial oocysts for use as "infected control". Moreover, chicks in a group of 3 birds were reared solely on the basal diet free from the drugs and without infection with oocysts for use as "uninfected control". The results were evaluated in the following manner. (A) The chicks were examined for signs of haemorrhage at days-4,5,6 and 7 after infection and the number of bloody droppings was used as a criterion; (B) The chicks were investigated for deaths at days-5,6,7 and 8 after infection; (C) The weight gain ratio for each group (the weight gain for each test group→the weight gain for the uninfected control group×100) at day-7 after infection was calculated; (D) At day-8 after infection, the birds were autopsied, and the caecal lesions as visually observed were scored against a 5-point scale, (−) through (+ + + +), by the procedure of Johnson and Reid as described in Experimental Parasitology 28, 30(1970). The results are set forth in Table-1.

Table 1

| Test item Group | No. of bloody droppings/bird Day- | | | | No. of deads Day- | | | | No. of birds At end/At start | Caecal lesion | | | | | Relative weight gain (%) |
|---|---|---|---|---|---|---|---|---|---|---|---|---|---|---|---|
| | 4 | 5 | 6 | 7 | 5 | 6 | 7 | 8 | | ++++ | +++ | ++ | + | − | |
| Compound 1 | 0 | 0 | 0 | 0 | 0 | 0 | 0 | 0 | 3/3 | | | | | 3 | 99.2 |
| Compound 2 | 0 | 0 | 0 | 0 | 0 | 0 | 0 | 0 | 3/3 | | | | 3 | | 87.5 |
| Uninfected control | 0 | 0 | 0 | 0 | 0 | 0 | 0 | 0 | 3/3 | | | | | 3 | 100.0 |
| Infected control | 5.3 | 9.6 | 8.6 | 2.0 | 0 | 1 | 0 | 0 | 2/3 | 2 | | | | | 54.3 |

Table 2

| Composition of Basal Diet | |
|---|---|
| Component | Weight percent |
| Cornmeal | 55.0 |
| Wheat bran | 5.0 |
| Soybean cake | 18.0 |
| Fish meal | 8.0 |
| Fish soluble | 3.0 |
| Alfalfa meal | 3.0 |
| Tallow complex | 5.7 |
| Calcium carbonate | 0.9 |
| Tricalcium phosphate | 0.7 |
| Sodium chloride | 0.25 |
| A-Feed E Beads* | 0.05 |
| B-Feed S* | 0.1 |
| Neominefeed C* | 0.05 |
| Vitamin B$_{12}$-T* | 0.05 |
| Extracted soybean meal | 0.2 |
| Total | 100.0 |

*Trade names [Distributed by Takeda Chemical Industries, Ltd. (Japan)]

EXPERIMENTAL DATA 2

Test materials and testing procedures (1) Test compounds
Compound 1: 9-(2-Chloro-6-fluorobenzyl)-6-methylaminopurine
Arprinocid[MK-302]: 6-Amino-9-(2-chloro-6-fluorobenzyl)purine [U.S. Pat. No. 3,846,426]

(2) Ratio of each test compound to feed
To aliquots of a starter ration (the composition is given in Table-2), there were added 0.01, 0.009, 0.008, 0.007 and 0.006 weight % of each test compound, respectively, as final concentrations.

(3) Testing procedures

The same procedures as those described in Experimental data 1, except for employing the chicks in groups of 9 birds, were repeated. The results are set forth in Table-3.

dish for 3 days at room temperature. The number of sporulated and non-sporulated oocysts was counted at least 3 times using a plankton counting chamber. In samples where only low oocyst counts were observed, the counting procedure was repeated 6 times. The percent ratio of sporulated oocysts to the sum of the counted oocysts was recorded. The results are set forth in Table-4.

Table 3

| Group | Test item Level in feed (%) | No. of bloody droppings/bird Day- 4 | 5 | 6 | 7 | No. of deads Day- 5 | 6 | 7 | 8 | No. of birds At end/ At start | Caecal lesion ++++ | +++ | ++ | + | − | Relative weight gain (%) |
|---|---|---|---|---|---|---|---|---|---|---|---|---|---|---|---|---|
| Compound 1 | 0.01 | 0 | 0 | 0 | 0 | 0 | 0 | 0 | 0 | 9/9 | | | | | 9 | 100.6 |
| | 0.009 | 0 | 0 | 0 | 0 | 0 | 0 | 0 | 0 | 9/9 | | | | | 9 | 99.7 |
| | 0.008 | 0 | 0 | 0 | 0 | 0 | 0 | 0 | 0 | 9/9 | | | | 2 | 7 | 104.8 |
| | 0.007 | 0 | 0.9 | 1.4 | 0.1 | 0 | 0 | 0 | 0 | 9/9 | | 3 | 2 | | 4 | 99.7 |
| | 0.006 | 0.2 | 4.5 | 1.9 | 0.1 | 0 | 0 | 0 | 0 | 9/9 | 2 | | 6 | 1 | | 86.7 |
| Arprinocid | 0.01 | 0 | 0 | 0 | 0 | 0 | 0 | 0 | 0 | 9/9 | | | | | 9 | 69.5 |
| | 0.009 | 0 | 0 | 0 | 0 | 0 | 0 | 0 | 0 | 9/9 | | | | | 9 | 78.3 |
| | 0.008 | 0 | 0 | 0.2 | 0 | 0 | 0 | 0 | 0 | 9/9 | | 1 | | 1 | 7 | 93.6 |
| | 0.007 | 0 | 0.8 | 1.1 | 0.2 | 0 | 0 | 0 | 0 | 9/9 | | 2 | 1 | 1 | 4 | 99.1 |
| | 0.006 | 0.1 | 2.3 | 1.9 | 0.1 | 0 | 0 | 0 | 0 | 9/9 | | 2 | 3 | 2 | 2 | 89.9 |
| Uninfected control | — | 0 | 0 | 0 | 0 | 0 | 0 | 0 | 0 | 9/9 | 0 | 0 | 0 | 0 | 9 | 100.0 |
| Infected control | — | 5.3 | 9.4 | 8.4 | 2.3 | 0 | 0 | 2 | 2 | 5/9 | 5 | | | | | 45.5 |

EXPERIMENTAL DATA 3

Test material and testing procedures (1) Test compound
Compound 1: 9-(2-Chloro-6-fluorobenzyl)-6-methylaminopurine.

(2) Ratio of the test compound to feed
The ratios of compound 1 were the same as those described in Experimental data 2.

(3) Testing procedures
The experimental procedure except for measuring the oocyst production and the sporulation was the same as those described in Experimental data 1 and 2.

At 8 days after the infection the birds were killed and caecum of each bird was excised. The caecal contents and scrapped mucous membrane were smeared on a slide glass and the production of oocysts of each bird was examined microscopically. When oocysts were not detected, whole caecal contents and the scrapped mucous membrane was suspended with a saturated salt solution and the existence of oocysts of the supernatant was re-examined microscopically after the suspension was centrifuged at 2000 rpm for 5 minutes.

The number of birds which showed oocyst production was recorded as the ratio to the tested birds of each group.

The oocysts from caecal collection were subjected to sporulation test in a manner as to be suspended in a 2% potassium dichromate solution and placed on the petri dish for 3 days at room temperature.

Table 4

| Group | Level in feed (%) | Test item Oocyst production (No. of oocyst-detected birds/tested birds) | Sporulation rate (%) |
|---|---|---|---|
| Compound 1 | 0.01 | 0/9 | — |
| | 0.009 | 0/9 | — |
| | 0.008 | 2/9 | 0 |
| | 0.007 | 5/9 | 0 |
| | 0.006 | 9/9 | 0 |
| Infected control | — | 9/9 | 85.2 |

EXPERIMENTAL DATA 4

Test material and testing procedures (1) Test compound
Compound 3: 9-(2-Chloro-6-fluorobenzyl)-6-dimethylaminopurine (2) Testing procedures
The procedures were the same as those described in Experimental data 1 and 3. The results are set forth in Table-5.

Table 5

| Test Item Group | Level in feed (%) | No. of bloody droppings/bird Day- 4 | 5 | 6 | 7 | No. of deads Day- 5 | 6 | 7 | 8 | No. of birds At end At start | Caecal lesion ++++ | +++ | ++ | + | − | Relative weight gain (%) | Oocyst production (No. of oocyst-detected birds/tested birds) | Sporulation rate (%) |
|---|---|---|---|---|---|---|---|---|---|---|---|---|---|---|---|---|---|---|
| Compound 3 | 0.01 | 0 | 0 | 0 | 0 | 0 | 0 | 0 | 0 | 3/3 | | | | | 3 | 92.0 | 0/3 | — |
| | 0.009 | 0 | 0 | 0 | 0 | 0 | 0 | 0 | 0 | 3/3 | | | | | 3 | 97.8 | 0/3 | — |
| | 0.008 | 0 | 0 | 0 | 0 | 0 | 0 | 0 | 0 | 3/3 | | | | | 3 | 101.6 | 0/3 | — |
| | 0.007 | 0 | 0 | 0 | 0 | 0 | 0 | 0 | 0 | 3/3 | | | | 2 | 1 | 104.0 | 1/3 | 0 |
| | 0.006 | 0 | 4.6 | 2.0 | 0 | 0 | 0 | 0 | 0 | 3/3 | | 2 | 1 | | | 91.9 | 3/3 | 1.0 |
| Uninfected control | — | 0 | 0 | 0 | 0 | 0 | 0 | 0 | 0 | 3/3 | | | | | 3 | 100.0 | 0/3 | — |
| Infected control | — | 5.0 | 10.0 | 9.0 | 5.0 | 0 | 0 | 1 | 0 | 2/3 | 2 | | | | | 48.8 | 2/2 | 85.0 |

EXAMPLE 1

(1) In 24 ml of N,N-dimethylacetamide was suspended 2.22 g of 6-amino-9-(2-chloro-6-fluorobenzyl)purine and, after 2.4 ml of methyl iodide was added, the suspension was stirred in the dark at room temperature for 10 hours and, then, allowed to stand overnight. To this reaction mixture was added ethanol and the resultant precipitate was collected by filtration and recrystallized from ethanol. By the above procedure there was obtained 2.09 g of 6-amino-9-(2-chloro-6-fluorobenzyl)-1-methylpurine hydriodide as colorless scales (yield 62%). m.p. Not less than 300° C. Elemental analysis; for $C_{13}H_{11}ClFN_5 \cdot HI$: Calcd. C, 37.21; H, 2.88; N, 16.69. Found C, 37.30; H, 2.83; N, 16.86.

(2) The compound obtained in (1) above (500 mg) was admixed with 200 ml of a 10% methanolic solution of sodium hydroxide and the mixture was stirred at room temperature for 5 hours and, then, allowed to stand for 3 days. The methanol was evaporated under reduced pressure, water was added to the residue and the resultant precipitate was recovered by filtration and recrystallized from ethanol. By the above procedure there was obtained 251 mg (yield 72%) of 9-(2-chloro-7-fluorobenzyl)-6-methylaminopurine as colorless needles, m.p. 184°–185° C.

Elemental analysis, for $C_{13}H_{11}ClFN_5$: Calcd. C, 53.53; H, 3.80; N, 24.01. Found C, 53.54; H, 3.63; N, 24.06.

EXAMPLE 2

A mixture of 940 mg of 6-chloro-9-(2,5-dichlorobenzyl)purine, 1.17 g of 40% aqueous methylamine and 75 ml of methanol was heated in a sealed tube at 100°–110° C. for 3 hours. After cooling, the mixture was concentrated to dryness under reduced pressure. To the residue was added water and the insolubles were recovered by filtration and recrystallized from ethanol. By the above procedure there was obtained 770 mg (yield 83%) of 9-(2,6-dichlorobenzyl)-6-methylaminopurine as needles melting at 224°–225° C.

Elemental analysis, for $C_{13}H_{11}Cl_2N_5$: Calcd, C, 50.67; H, 3.60; N, 22.73. Found C, 50.58; H, 3.54; N, 22.72.

EXAMPLE 3

(1) 6-Amino-9-(2,6-dichlorobenzyl)purine (588 mg), 0.7 ml of methyl iodide and 7 ml of N,N-dimethylacetamide were treated in the same manner as Example 1, whereby 401 mg (yield 47%) of 6-amino-9-(2,6-dichlorobenzyl)-1-methylpurine hydriodide was obtained as colorless needles melting at no less than 300° C.

(2) The compound obtained in (1) above (218 mg) was further treated in the same manner as Example 1 to obtain 91 mg (yield 59%) of 9-(2,6-dichlorobenzyl)-6-methylaminopurine as needles.

EXAMPLE 4

6-Chloro-9-(2,6-dichlorobenzyl)purine 627 mg, 2.2 g of 20% methanolic dimethylamine and 50 ml of methanol were treated in the same manner as Example 2. By the above procedure there was obtained 504 mg (yield 79%) of 9-(2,6-dichlorobenzyl)-6-dimethylaminopurine as colorless needles, m.p. 174°–175° C.

Elemental analysis, for $C_{14}H_{13}Cl_2N_5$: Calcd. C, 52.19; H, 4.08; N, 21.74. Found C, 52.16; H, 4.46; N, 21.60.

EXAMPLE 5

6-Chloro-9-(2,6-dichlorobenzyl)purine (314 mg), 322 mg of 70% aqueous ethylamine and 25 ml of methanol were treated in the same manner as Example 2, whereby 255 mg (yield 79%) of 9-(2,6-dichlorobenzyl)-6-ethylaminopurine was obtained as needles melting at 222°–223° C.

Elemental analysis, for $C_{14}H_{13}Cl_2N_5$: Calcd. C, 52.19; H, 4.08; N, 21.74. Found: C, 51.95; H, 3.91; N, 21.46.

EXAMPLE 6

6-Chloro-9-(2,6-dichlorobenzyl)purine (314 mg), 365 mg of diethylamine and 25 ml of methanol were treated in the same manner as Example 2, whereby 212 mg (yield 61%) of 9-(2,6-dichlorobenzyl)-6-diethylaminopurine was obtained as needles melting at 140°–141° C.

Elemental analysis, for $C_{16}H_{17}Cl_2N_5$: Calcd. C, 54.87; H, 4.89; N, 20.00. Found: C, 55.17; H, 4.88; N, 19.94.

EXAMPLE 7

6-Chloro-9-(2,6-dichlorobenzyl)purine (314 mg), 296 mg of isopropylamine and 25 ml of methanol were treated in the same manner as Example 2 and recrystallized from aqueous ethanol to obtain 276 mg (yield 79%) of 9-(2,6-dichlorobenzyl)-6-isopropylaminopurine as colorless needles melting at 109°–110° C.

Elemental analysis, for $C_{15}H_{15}Cl_2N_5 \cdot \frac{3}{4}H_2O$: Calcd. C, 51.51; H, 4.75; N, 20.02. Found: C, 51.59; H, 4.52; N, 19.85.

EXAMPLE 8

6-Chloro-9-(2,6-dichlorobenzyl)purine (314 mg), 286 mg of allylamine and 25 ml of methanol were treated in the same manner as Example 2, whereby 271 mg (yield 81%) of 6-allylamino-9-(2,6-dichlorobenzyl)purine was obtained as colorless prisms melting at 202.5°–204° C.

Elemental analysis, for $C_{15}H_{13}Cl_2N_5$: Calcd. C, 53.91; H, 3.92; N, 20.95. Found C, 53.80; H, 3.77; N, 20.98.

EXAMPLE 9

To a mixture of 7.45 g of 6-methylaminopurine, 6.9 g of potassium carbonate and 250 ml of N,N-dimethylacetamide was added 17.9 g of 2-chloro-6-fluorobenzyl chloride, and the resultant mixture was allowed to react at 110° C. for 6 hours with stirring. After cooling, the reaction mixture was filtered to remove insoluble materials and the filtrate was concentrated to dryness under reduced pressure. Upon addition of water to the resultant residue, the formed precipitate was collected by filtration and recrystallized from ethanol to give 9.08 g of 9-(2-chloro-6-fluorobenzyl)-6-methylaminopurine as colorless needles (yield: 63%), m.p. 188°–190° C. Nuclear magnetic resonance (NMR) spectrum of this product is identical with that of the corresponding compound synthesized in Example 1.

EXAMPLE 10

In a procedure analogous to that of Example 9, by using 1.49 g of 6-methylaminopurine, 1.38 g of potassium carbonate, 50 ml of N,N-dimethylacetamide and 3.92 g of 2,6-dichlorobenzyl chloride, there was obtained 1.9 g of 9-(2,6-dichlorobenzyl)-6-methylaminopurine as colorless needles (yield: 62%), m.p. 219°–220° C. NMR spectrum of this product is identical with that of the corresponding compound synthesized in Example 2.

EXAMPLE 11

In a procedure analogous to that of Example 9, by using 1.63 g of 6-dimethylaminopurine, 1.38 g of potassium carbonate, 50 ml of N,N-dimethylacetamide and 3.58 g of 2-chloro-6-fluorobenzyl chloride, there was obtained 1.9 g of 9-(2-chloro-6-fluorobenzyl)-6-dimethylaminopurine as colorless needles (yield: 62%); m.p. 134°–135° C.

Elemental analysis, for $C_{14}H_{13}ClFN_5$:
Calcd. C, 55.00; H, 4.29; N, 22.91. Found C, 54.91; H, 4.23; N, 22.86.

EXAMPLE 12

In a procedure analogous to that of Example 9, by using 1.63 g of 6-ethylaminopurine, 1.38 g of potassium carbonate, 50 ml of N,N-dimethylacetamide and 3.58 g of 2-chloro-6-fluorobenzyl chloride, there was obtained 1.04 g of 9-(2-chloro-6-fluorobenzyl)-6-ethylaminopurine as colorless needles (yield: 34%), m.p. 175°–176° C.

Elemental analysis, for $C_{14}H_{13}ClFN_5$: Calcd. C, 55.00; H, 4.29; N, 22.91. Found C, 54.66; H, 4.05; N, 22.90.

EXAMPLE 13

In a procedure analogous to that of Example 9, by using 1.77 g of 6-n-propylaminopurine, 1.38 g of potassium carbonate, 50 ml of N,N-dimethylacetamide and 3.58 g of 2-chloro-6-fluorobenzyl chloride, there was obtained 1.89 g of 9-(2-chloro-6-fluorobenzyl)-6-n-propylaminopurine as colorless needles (yield: 59%), m.p. 166°–167° C.

Elemental analysis, for $C_{15}H_{15}ClFN_5$: Calcd. C, 56.34; H, 4.73; N, 21.90. Found C, 56.12; H, 4.59; N, 21.67.

EXAMPLE 14

In a procedure analogous to that of Example 9, by using 1.75 g of 6-allylaminopurine, 1.38 g of potassium carbonate, 50 ml of N,N-dimethylacetamide and 3.58 g of 2-chloro-6-fluorobenzyl chloride, there was obtained 1.84 g of 6-allylamino-9-(2-chloro-6-fluorobenzyl)purine as colorless needles (yield: 58%), m.p. 163°–164° C.

Elemental analysis, for $C_{15}H_{13}ClFN_5$: Calcd. C, 56.70; H, 4.12; N, 22.04. Found C, 56.43; H, 3.92; N, 22.09.

We claim:

1. A compound of the formula:

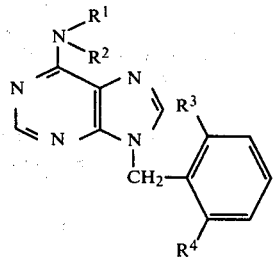

wherein $R^1$ is hydrogen or alkyl of 1 to 3 carbon atoms, $R^2$ is alkyl of 1 to 3 carbon atoms or allyl, and $R^3$ and $R^4$, respectively, mean halogen, or an acid addition salt thereof.

2. A compound according to claim 1, wherein $R^1$ is hydrogen or methyl, and $R^2$ is methyl.

3. A compound according to claim 1 or 2, wherein $R^3$ is chlorine and $R^4$ is fluorine.

4. The compound according to claim 1, which is 9-(2-chloro-6-fluorobenzyl)-6-methylaminopurine.

5. The compound according to claim 1, which is 9-(2-chloro-6-fluorobenzyl)-6-dimethylaminopurine.

6. The compound according to claim 1, which is 9-(2-chloro-6-fluorobenzyl)-6-ethylaminopurine.

7. The compound according to claim 1, which is 9-(2-chloro-6-fluorobenzyl)-6-n-propylaminopurine.

8. The compound according to claim 1, which is 9-(2,6-dichlorobenzyl)-6-methylaminopurine.

9. The compound according to claim 1, which is 9-(2,6-dichlorobenzyl)-6-dimethylaminopurine.

10. An anticoccidial composition comprising as an active ingredient an effective amount of a compound of the formula:

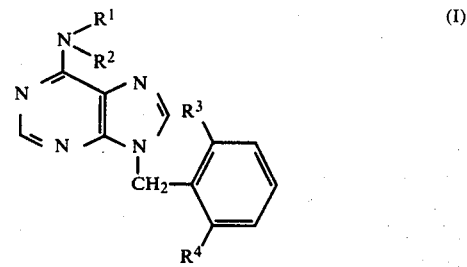

wherein $R^1$ is hydrogen or alkyl of 1 to 3 carbon atoms, $R^2$ is alkyl of 1 to 3 carbon atoms or allyl, and $R^3$ and $R^4$, respectively, mean halogen, or a physiologically acceptable acid addition salt thereof, and a physiologically acceptable carrier or diluent therefor.

11. An anticoccidial composition according to claim 10, which is a poultry ration.

12. An anticoccidial composition according to claim 10, wherein $R^1$ of the compound (I) is hydrogen or methyl, and $R^2$ of the compound (I) is methyl.

13. An anticoccidial composition according to claim 10 or 12, wherein $R^3$ of the compound (I) is chlorine and $R^4$ of the compound (I) is fluorine.

14. An anticoccidial composition according to claim 10, wherein the compound (I) is 9-(2-chloro-6-fluorobenzyl)-6-methylaminopurine.

15. An anticoccidial composition according to claim 10, wherein the compound (I) is 9-(2-chloro-6-fluorobenzyl)-6-dimethylaminopurine.

16. An anticoccidial composition according to claim 10, wherein the compound (I) is 9-(2-chloro-6-fluorobenzyl)-6-ethylaminopurine.

17. An anticoccidial composition according to claim 10, wherein the compound (I) is 9-(2-chloro-6-fluorobenzyl)-6-n-propylaminopurine.

18. An anticoccidial composition according to claim 10, wherein the compound (I) is 9-(2,6-dichlorobenzyl)-6-methylaminopurine.

19. An anticoccidial composition according to claim 10, wherein the compound (I) is 9-(2,6-dichlorobenzyl)-6-dimethylaminopurine.

20. A method for treating coccidiosis in poultry or domestic animals which comprises orally administering to the poultry or the domestic animals an effective amount of a compound of the formula:

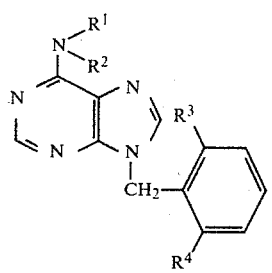
(I)
wherein $R^1$ is hydrogen or alkyl of 1 to 3 carbon atoms, $R^2$ is alkyl of 1 to 3 carbon atoms or allyl, and $R^3$ and $R^4$, respectively, mean halogen, or a physiologically acceptable acid addition salt thereof.
* * * * *